(12) United States Patent
Chen et al.

(10) Patent No.: US 7,880,139 B2
(45) Date of Patent: Feb. 1, 2011

(54) METHOD AND APPARATUS OF UNIFORM GAS-PHASE MOLECULAR MATRIX DEPOSITION FOR IMAGING MASS SPECTROMETRY

(75) Inventors: Yanfeng Chen, Atlanta, GA (US); M. Cameron Sullards, Atlanta, GA (US); Thomas M. Orlando, Atlanta, GA (US); Joseph A. Hankin, Denver, CO (US); Robert C. Murphy, Denver, CO (US); Robert M. Barkley, Boulder, CO (US)

(73) Assignee: Georgia Tech Research Corporation, Atlanta, GA (US)

( * ) Notice: Subject to any disclaimer, the term of this patent is extended or adjusted under 35 U.S.C. 154(b) by 120 days.

(21) Appl. No.: 12/154,912

(22) Filed: May 28, 2008

(65) Prior Publication Data
US 2010/0090099 A1     Apr. 15, 2010

Related U.S. Application Data

(60) Provisional application No. 60/941,026, filed on May 31, 2007.

(51) Int. Cl.
*H01J 49/04* (2006.01)
(52) U.S. Cl. .................... 250/288; 250/282
(58) Field of Classification Search ........... None
See application file for complete search history.

(56) References Cited

U.S. PATENT DOCUMENTS

| | | |
|---|---|---|
| 5,643,800 A | 7/1997 | Tarantino et al. |
| 5,854,486 A | 12/1998 | Dreyfus |

(Continued)

OTHER PUBLICATIONS

M. Stoeckli, P. Chaurand, D.E., Hallahan, and R.M. Caprioli, "Imaging Mass Spectrometry: A New Technology for the Analysis of Protein Expression in Mammalian Tissue", Nat. Med. 7, 2001, pp. 493-496.

(Continued)

*Primary Examiner*—Jack I Berman
(74) *Attorney, Agent, or Firm*—Thomas, Kayden, Horstemeyer & Risley, LLP

(57) ABSTRACT

Disclosed are apparatus and methods for depositing solvent-free molecules on surfaces of samples, with particular application to imaging mass spectrometry. A vacuum chamber is configured to have controllable matrix translation apparatus for controlling the position of one or more solvent-free matrices within the chamber. Sublimation apparatus is used to sublimate molecules from the solid phase matrices. One or more samples are placed separately from the solvent-free matrices within the chamber. Condensation apparatus individually cools the samples to deposit sublimated molecules on the samples. Controllable sample translation apparatus is used to control the position of the samples within the chamber. Rotatable sample holding apparatus may be used to hold and move the samples to allow deposition of molecules on multiple samples at substantially the same time. Rotatable matrix holding apparatus may also be used to hold and move a plurality of matrices to create a homogenous mixture of molecules that are deposited onto one or more samples. As surface characterization system may be used to monitor deposition of the molecules to determine their thickness and roughness. A computer may be configured to control the matrix translation apparatus, the sublimation apparatus, the condensation apparatus, and the sample translation apparatus to provide for automated deposition of solvent-free molecules on the samples.

18 Claims, 5 Drawing Sheets

U.S. PATENT DOCUMENTS

| | | | |
|---|---|---|---|
| 6,104,028 | A | 8/2000 | Hunter et al. |
| 7,405,395 | B2 * | 7/2008 | Ellson et al. ................ 250/288 |
| 2010/0038529 | A1 * | 2/2010 | Sato et al. .................. 250/282 |
| 2010/0176288 | A1 * | 7/2010 | Barnes et al. ............... 250/282 |

OTHER PUBLICATIONS

R. Lemair, M. Wisztorski, A. Desmons, J.C. Tabet, R. Day, et al., "MALDI-MS Direct Tissue Analysis of proteins: Improving Signal Sensitivity Using Organic Treatments", Anal. Chem. 78, 2006, pp. 7145-7153.

3. J.A. Hankin, R.M. Barkley, R.C. Murphy, "Sublimation as a Method of Matrix Applications for Mass Spectrometric Imaging", J. Am. Soc. Mass Spectr., Jun. 30, 2007, pp. 1646-1652.

M. Stoekli, et al., "Imaging mass spectrometry: A new technology for the analysis of protein expression in mammalian tissues", Nat Med, 7, 2001, 493-496.

R. Lemair, et al., "MALDI-MS Direct Tissue Analysis of Proteins: Improving Signal Sensitivity Using Organic Treatments", Anal Chem, 78, 2006, 7145-7153.

* cited by examiner

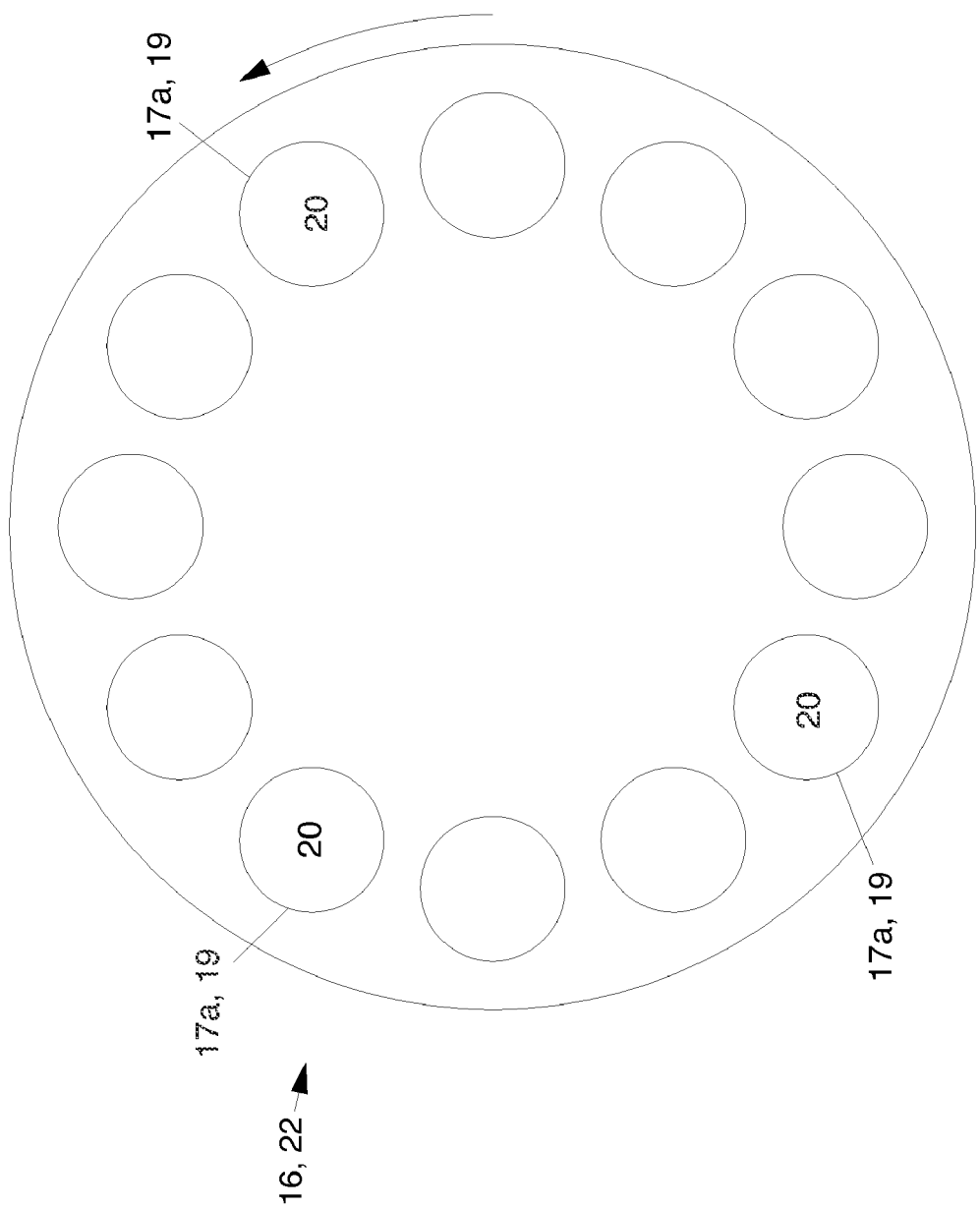

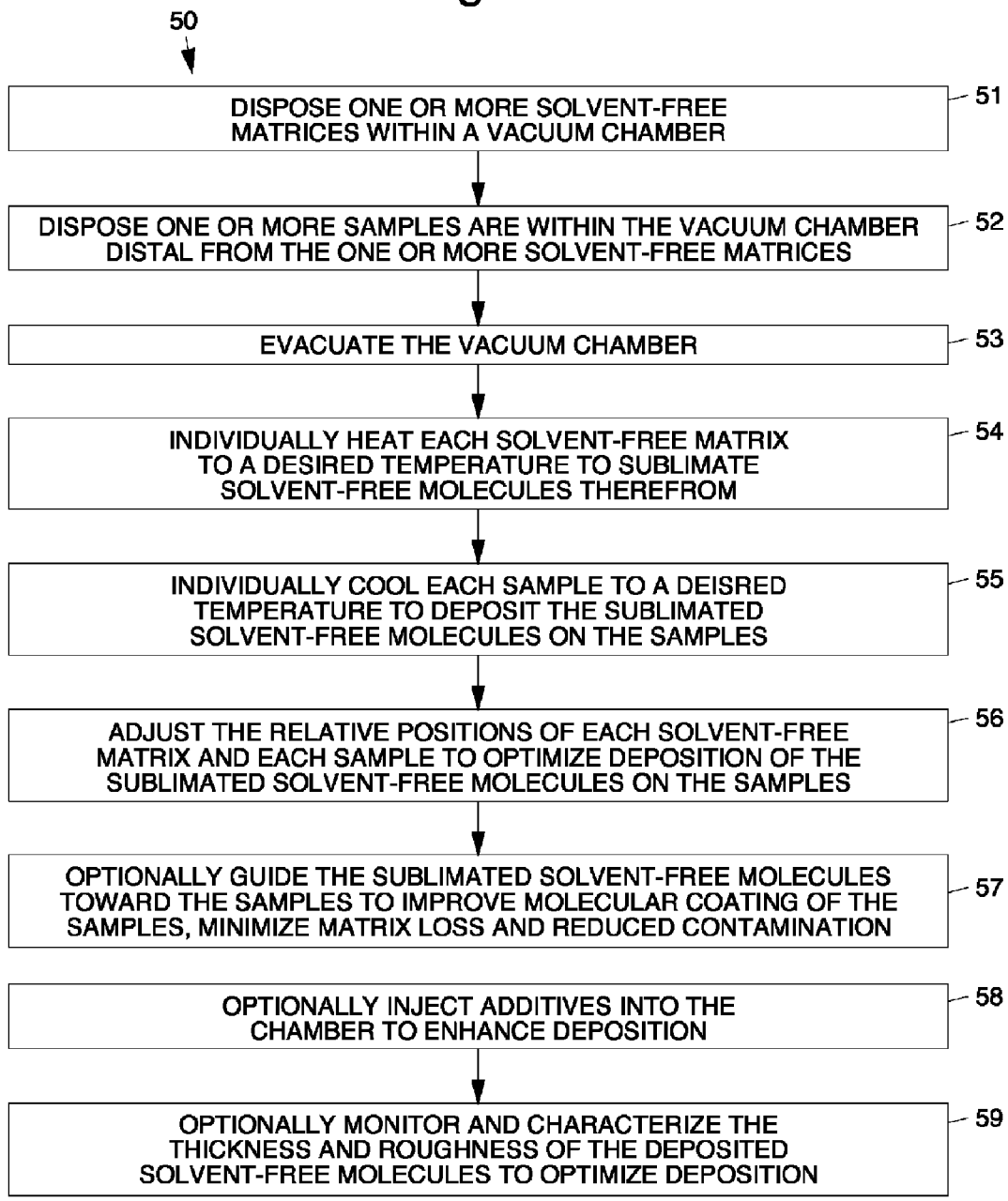

US 7,880,139 B2

METHOD AND APPARATUS OF UNIFORM GAS-PHASE MOLECULAR MATRIX DEPOSITION FOR IMAGING MASS SPECTROMETRY

This application claims the benefit of U.S. Provisional Application No. 60/941,026, filed May 31, 2007.

BACKGROUND

The present invention relates generally to mass spectrometry, and more particularly to solvent-free matrix deposition apparatus and methods using sublimation for imaging mass spectrometry.

Matrix-assisted laser desorption/ionization imaging mass spectrometry (MALDI-IMS) is a revolutionary and emerging technique for profiling and mapping biomolecules and studying related biological processes directly from the samples. MALDI-IMS is discussed by M. Stoeckli, et al., in "Imaging mass spectrometry: A new technology for the analysis of protein expression in mammalian tissues", Nat Med, 7, 2001, 493-496, for example.

Based on its potential of simultaneously providing identification and spatial localization of most molecules of interest in complicated biological samples such as tissues and cells, imaging mass spectrometry has been recognized as a promising tool for numerous applications including peptide/protein, lipid, metabolite analysis, biomarker discovery, drug biodistribution monitoring, molecular mechanism investigation, etc. This is discussed by R. Lemair, et al., in "MALDI-MS Direct Tissue. Analysis of Proteins: Improving Signal Sensitivity Using Organic Treatments", Anal Chem, 78, 2006, 7145-7153, for example.

Uniformly coating the matrix onto sample surfaces is one of the most critical experimental factors in MALDI-IMS. The reproducibility and quality of MALDI imaging analyses are greatly affected by the size and homogeneity of the matrix cluster/crystal as well as the inevitable analyte spreading caused by solvents used for matrix deposition.

Currently, there are two generally-used methods for matrix deposition: spraying and spotting. Both of them have a common problem of using solvents as media to transfer the matrix onto the sample surface. It is impossible to avoid lateral movement of the analytes with the existence of solvents, which reduces the signal intensity and resolution of molecular imaging. In addition, spraying and spotting techniques have other limitations, such as high irreproducibility, poor control of matrix/analyte incorporation, slow coating process, and alkali metal contamination (Nat or K).

A number of U.S. patents have been issued relating to ionization mass spectrometry. U.S. Pat. No. 5,643,800 entitled "Method of preparing a sample for analysis by laser desorption ionization mass spectrometry" issued Jul. 1, 1997, U.S. Pat. No. 5,854,486 entitled "Method and apparatus for MALDI mass spectrometry" issued Dec. 29, 1998, and U.S. Pat. No. 6,104,028 entitled "Volatile matrices for matrix-assisted laser desorption/ionization mass spectrometry" issued Aug. 15, 2000.

As evidenced by its abstract, U.S. Pat. No. 5,643,800 discloses "a sample preparation system and method that can be used with all types of analyte materials, that produces homogeneously deposited crystals across a sample surface, and that lends itself to automation. In this system and method, analyte crystallization is caused by lyophilization. A homogeneous analyte/solvent mixture is placed on a sample surface. The mixture is frozen, then the solvent is sublimated through the application of a vacuum. A homogenous distribution of analyte crystals across the sample surface results." Thus, U.S. Pat. No. 5,643,800 discloses sublimation of a solvent that has been placed on a surface to create a crystalline surface on a sample.

As evidenced by its abstract, U.S. Pat. No. 5,854,486 discloses that a "thin uniform film of matrix material is deposited from the gas phase on to a substrate for use in Matrix Assisted Laser Desorption and Ionization (MALDI) spectroscopy. The thin uniform film of material may be overcoated with another film of material which has a higher vapor pressure than the matrix material to prevent the matrix material from evaporating during storage and during substantial time in the vacuum environment of the mass spectrometer." The Summary of the Invention section of U.S. Pat. No. 5,854,486 states that "A thin, uniform film of matrix material is deposited on a substrate by sublimation of the solid matrix material or by other vapor deposition methods." U.S. Pat. No. 5,854,486 discloses a column 5, lines 20-25 that "The analyte material 50 may be deposited on the matrix material of layer 20 by a number of techniques. The easiest of such techniques is merely to drop a drop of solution containing the analyte material, a volatile solvent, and optionally matrix material on the surface of the layer 20 and to allow the volatile component of the solution to evaporate."

The abstract of U.S. Pat. No. 6,104,028 states that a "sample preparation method is disclosed for volatilization and mass spectrometric analysis of nonvolatile high molecular weight molecules. Photoabsorbing molecules having significant sublimation rates at room temperature under vacuum, and preferably containing hydroxy functionalities, are disclosed for use as matrices in matrix-assisted laser desorption/ionization mass spectrometry. The samples are typically cooled in the mass spectrometer to temperatures significantly below room temperature." The Summary of the Invention section of U.S. Pat. No. 6,104,028 discloses "a method for determining the mass of a large organic molecule" and that the sample preparation method uses "liquids or low sublimation temperature solids as matrices because such systems generally enable lower desorption/ionization temperatures." However, U.S. Pat. No. 6,104,028 discloses that "In creating the matrix:molecule mixture, for example, by dissolving the large organic molecule in a solution containing the matrix, one of skill in the art will understand that the solution containing the matrix may generally contain one or more solvents."

However, none of the above-cited patents discloses or suggests formation of a solvent-free matrix using sublimation techniques. In addition, there are no conventional molecular matrix deposition systems that have matrix (source) and sample (target) movement systems or stages for optimizing sublimation-condensation position and mixed matrix deposition. Furthermore, no conventional molecular matrix deposition system employs apparatus that permits substantially homogeneous deposition of molecules from multiple matrices on one or multiple samples. Finally, no conventional molecular matrix deposition system employs apparatus that permits deposition of matrix molecules on multiple samples at substantially the same time.

It would be desirable to overcome the limitations offered by conventional matrix deposition approaches. It would be desirable to have solvent-free matrix deposition apparatus and methods for use in imaging mass spectrometry and other surface coating processes. It would be desirable to have apparatus and methods that provide uniform gas-phase molecular solvent-free matrix deposition for imaging mass spectrometry and other surface coating processes. It would be desirable to have apparatus and methods that form a solvent-free matrix on a sample using sublimation techniques. It would be desirable to have apparatus and methods that advantageously employ uniform gas-phase molecular solvent-free matrix deposition to coat surfaces of materials.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 1a illustrates exemplary rotatable matrix and sample holding apparatus that may be employed in the deposition apparatus shown in FIG. 1;

FIG. 3 is a flow diagram that illustrates an exemplary solvent-free matrix deposition method.

DETAILED DESCRIPTION

Figure 1:
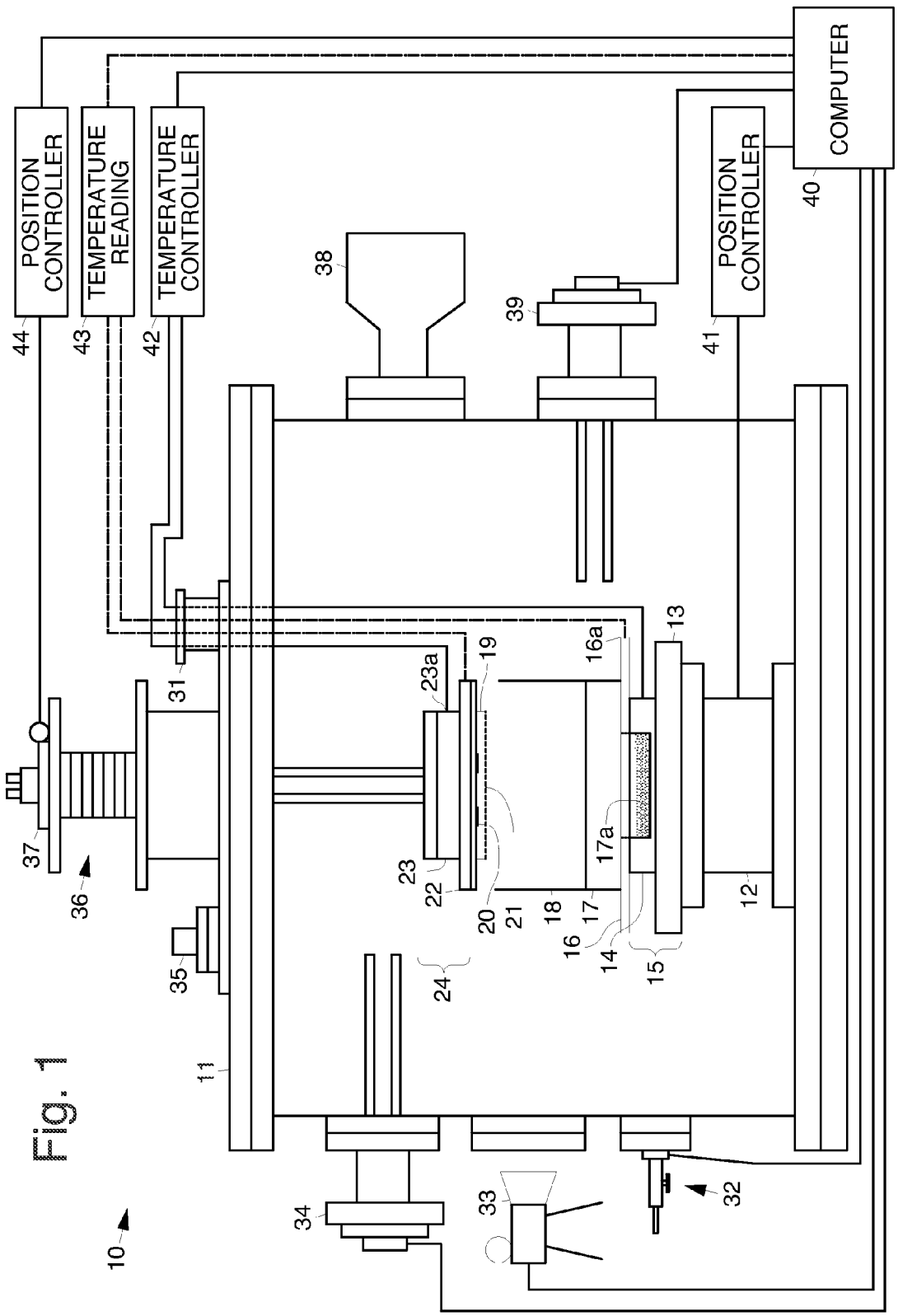
FIG. 1 illustrates exemplary solvent-free matrix vapor deposition apparatus.

Disclosed are universal solvent-free (i.e., powder) matrix deposition apparatus and methods for coating samples with molecules that are particularly useful in imaging mass spectrometry. The apparatus and methods may be used in numerous applications including peptide/protein, lipid, metabolite analysis, biomarker discovery, drug biodistribution monitoring, disease stage assessment, molecular mechanism investigation, and the like. The apparatus and related methods advantageously employ uniform gas-phase molecular solvent-free matrix deposition.

Deposition of molecules from solvent-free matrices provided by the apparatus and methods greatly improves spatial resolution and detection sensitivity. The apparatus and methods automatically provide precise control of matrix deposition. The apparatus and methods provide uniform high-throughput deposition of matrix mixtures onto samples. The apparatus and methods provide high-throughput matrix deposition onto large samples or multiple samples at substantially the same time.

The apparatus and methods embody matrix and sample position control systems or stages that optimize sublimation-condensation position and mixed matrix deposition. The apparatus and methods may embody a rotatable matrix holding apparatus that permits substantially homogeneous deposition of molecules from multiple matrices onto one or multiple samples. This overcomes the shortcoming of using liquid (solvent) matrices which produce an uneven coating and introduce undesirable sodium (Na) and potassium (K) into the coating. The apparatus and methods may also employ a rotatable sample holding apparatus that permits deposition of matrix molecules on multiple samples at substantially the same time.

More particularly, disclosed herein are methods and apparatus for depositing uniform layers of matrix molecules on surfaces, such as biological and surfaces for analysis of cells and tissues using mass spectrometric imaging techniques. The improved quality of the deposited molecules greatly improves molecular imaging of samples using mass spectrometry. The apparatus and methods minimize analyte diffusion, simplify sample preparation, increase spatial resolution, control matrix/analyte mixing and optimize the signal intensity attainable by imaging mass spectrometers.

The methods and apparatus embody the use of gas-phase molecular sublimation and condensation to apply a fine and even layer of molecules of a solvent-free matrix on sample surfaces. The methods and apparatus also control sample delivery, control matrix delivery through adjustments of quantity, sample position, film coating pattern, condensation condition, sublimation condition, vapor dosage, vacuum level, surface characterization and process automation.

Using the apparatus and methods, the matrix molecules are evenly deposited on sample surfaces with optimized thickness, while analyte diffusion and other effects caused by conventional solvent typically applied to the sample are eliminated. This approach may be used with essentially any solvent-free matrix, sample, and instrument. It overcomes the common problems of conventional matrix coating protocols and can be easily integrated into mass spectrometry technology to provide sensitive, reproducible, fast, and direct profiling and mapping of molecules in most biological systems with high spatial resolution.

The present inventors have found that application of molecules from a solvent-free matrix to a sample using sublimation-condensation overcome many of the shortcomings of conventional matrix deposition approaches. The disclosed methods and apparatus controls all variables for matrix deposition onto samples as vapor without the use of solvents. The methods and apparatus utilize controls for vacuum, heat, condensation, sample positioning, and patterning of deposition as well as practical attachments for a variety of sample plates commonly used for MALDI applications.

The use of matrix and sample position control systems optimizes sublimation-condensation position of the sample. The use of multiple matrix sources to create a homogenous mixture of multiple different molecules permits mixed matrix deposition onto samples. In particular, the use of the rotatable matrix holding apparatus permits substantially homogeneous deposition of molecules from multiple matrices onto one or multiple samples. The use of the rotatable sample holding apparatus permits deposition of matrix molecules onto multiple samples at substantially the same time.

The disclosed methods and apparatus thus facilitates fast, simple, and reproducible molecular deposition of matrix molecules on biological surfaces using a simple operation to yield excellent images of the localization of biomolecules. The apparatus and methods disclosed herein may also be used in applications other than imaging mass spectrometry, such as film growth, surface modification, and molecular printing for optimized performances.

Referring to the drawing figures, FIG. 1 illustrates exemplary solvent-free matrix vapor deposition apparatus 10. FIG. 1 also illustrates an experimental protocol for uniform molecular deposition based on sublimation. However, it is to be understood that other configurations of components making up the apparatus 10 shown in FIG. 1 may be employed to implement the principles disclosed herein. Therefore, it is to be understood that the embodiment shown in FIG. 1 should not limit the scope of the apparatus 10 and methods 50 (FIG. 3) disclosed herein.

As is shown in FIG. 1, the exemplary solvent-free matrix vapor deposition apparatus 10 comprises a processing chamber 11 or housing 11. An XYZ translation stage 12 (positioning stage 12) may be disposed on a base or bottom plate of the processing chamber 11. The XYZ translation stage 12 is coupled to an XYZ position controller 41.

A thermal insulation layer 13 is disposed on the XYZ translation stage 12. A heating stage 14 is disposed on the thermal insulation layer 13. The heating stage 14 is coupled by way of an electrical connector 31 that extends through the processing chamber 11 to a heating temperature controller 42. A sublimation system 15 is formed by the thermal insulation layer 13 and the heating stage 14. The sublimation system 15 converts a powered, solvent-free, sample 20 directly into a gas without passing through an intermediate liquid phase.

In one embodiment, a dock 16 or matrix holding apparatus 16 comprising a temperature readout 16a is disposed above the heating stage 14. The temperature readout 16a coupled by way of the electrical connector 31 to provide a heating temperature reading 43. A matrix container 17 is held by the dock 16 or matrix holding apparatus 16 above the sublimation system 15. The matrix container 17 holds a sample of solvent-free matrix material 17a.

In another embodiment, and with reference to FIG. 1a, a rotatable matrix holding apparatus 16 may be used in place of the single dock 16 to hold and rotate a plurality of matrix containers 17 and plurality of solvent-free matrices 17a above the sublimation system 15. A plurality of different heating plates 14 or stages 14 are respectively disposed beneath each container 17 held by the rotatable matrix holding apparatus 16 so that individual sublimation temperatures can be accurately controlled for each matrix. A motor (not shown) may be used to rotate the rotatable matrix holding apparatus 16 (indicated by the arrow to the right of the rotatable matrix holding apparatus 16). The use of multiple matrices 17a that are rotated within the chamber 11 by the rotatable matrix holding apparatus 16 create a homogenous mixture of different molecules substantially within the confines of the guiding system 18 and permits mixed matrix deposition onto one or more samples 20.

A molecule guiding system 18 is disposed above the matrix container 17. The molecule guiding system 18 provides for improved molecular coating, minimum matrix loss and reduced device contamination because it keeps the sublimated matrix molecules in a relatively confined space within the chamber 11 so that they more efficiently deposit on the sample 20.

A masking system 21 is disposed between the molecule guiding system 18 and a sample adapter 19 containing a sample 20. The masking system 21 is used to pattern deposition of the solvent-free molecules on the sample 20 and provide for selected region deposition of the solvent-free molecules on the sample 20.

In one embodiment, a sample holding apparatus 22 is disposed above the sample adapter 19 and holds the sample adapter 19. The sample holding apparatus 22 comprises a cooling temperature readout 22 that is coupled by way of the electrical connector 31 to provide a cooling temperature reading 43.

In another embodiment, and with reference to FIG. 1a, a rotatable sample holding apparatus 22 is used to hold multiple sample chambers 19, that permits deposition of matrix molecules on multiple samples 20 at substantially the same time. Multiple cooling plates 23 are respectively disposed adjacent to the multiple sample adapters 19 so that individual cooling temperatures can be accurately controlled for each sample 20.

The rotatable sample holding apparatus 22 is rotated while the molecules are sublimated and deposited on each sample 20 as it passes by the guiding system 18. A motor (not shown) may be used to rotate the rotatable sample holding apparatus 22 (indicated by the arrow to the right of the rotatable sample holding apparatus 22 in FIG. 1a).

A cooling plate 23 or stage 23 is disposed above the sample holding apparatus 22. The cooling plate 23 or stage 23 is connected by way of the electrical connector 31 to the temperature controller 42. Cooling lines 23a extend through the top plate of the processing chamber 11 through a cooling liquid feedthrough 37 that pass through a sample positioning system 36 or stage 36 that permits the flow of coolant to and from the cooling plate 23 or stage 23 to assist in dissipating heat from the cooling stage 23. It is to be understood that the sample positioning system 36 may be a rotational stage or a second XYZ translational stage that permits controlled movement of the position of the sample 20 to assist in providing optimized deposition parameters.

The first and second temperature readouts 16a, 22, are connected to a computer 40 to provide the first and second temperature readings 43 thereto. An output of the temperature controller 42 is connected to the computer 40. An output of the XYZ position controller 41 is connected to the computer 40.

The processing chamber 11 has a dosing line/vacuum control pumping system 32, or dosing system 32, that is connected to the computer 40. Typical vacuum pumps used to evacuate the vacuum chamber 11 normally cannot accurately control the vacuum within the chamber 11. The use of the dosing system 32 allows precise control of the pressure in the chamber 11 and permits addition of desired substances into the chamber 11 to enhance matrix deposition The processing chamber 11 has a surface characterization system 33 that may be used to monitor the thickness and roughness of the surface deposited on the sample 20. The surface characterization system 33 may be used to monitor and optimize deposition of matrix molecules on the sample 20.

The processing chamber 11 has a sample handling system 34, or sample transfer system 34, that is connected to the computer 40 and which allows an operator to insert and remove samples from the sample chamber 19 under the control of the computer 40.

A vacuum readout device 35 is provided on the processing chamber 11 which allows an operator to determine the amount of vacuum that exists within the processing chamber 11. The sample positioning system 36 or rotation stage 36 is disposed adjacent the top of the processing chamber 11 and is coupled to a sample position controller 44. The sample position controller 44 is connected to the computer 40 to allow control of the position of the cooling plate 23 or stage 23 and sample 20 to optimize deposition parameters. The surface of the sample 20 must be cooled in a controlled fashion in conjunction with the amount of heat provided by the sublimation system 15 in order to properly deposit the molecules on its surface.

A vacuum pumping system 38 with a cold trap is coupled to the processing chamber 11 to precisely control the pressure within the housing 11. It provides proper pressures for matrix deposition or fast surface cleaning. The processing chamber 11 has a matrix handling system 39, or matrix transfer system 39, that is connected to the computer 40 and which allows manipulate the solvent-free matrix under control of the computer 40.

Thus, the processing chamber 11 comprises a vacuum system equipped with multiple manipulation systems 12, 36 (i.e., the XYZ translation stage 12 and the sample positioning system 36). The cooling stage 23 and heating stage 14 are built into the chamber 11 that control sublimation and condensation processes. The heating stage 14 includes the matrix holding apparatus 16 which holds matrix containers 17. Each matrix holding apparatus 16 sits on its own heating plate 14 or stage 14 which is coupled to a separate temperature controller 42 (temperature control module 42) that precisely heats the matrix container 17 to a specified temperature in the range of 25 to 600° C. All heating components are placed on the XYZ translation stage 12 at the bottom of the chamber 11. The cooling stage 23 may have a single sample chamber 19 coupled to it, or multiple sample adapters 19 or holders 19 coupled to it to provide for simultaneous deposition of matrix molecules on multiple samples 20. The multiple sample holders 19 are respectively attached to multiple cooling plates 23 to provide accurate cooling in the temperature range of −70 to 70° C. Each sample holder 19 is mounted to a cooling plate 23 with good thermal conductivity.

The masking system 21 can controllably place masks in front of the samples 20 for patterning of matrix deposition or spot-selecting deposition of molecules. All cooling components are connected to the rotation stage 36 (sample positioning system 36) which has rotational (or XYZ) movement capability and the cooling liquid feedthrough 37 to provide for cooling liquid circulation through the cooling plate 23 or stage 23.

The samples 20 can be aligned to matrix containers 17 for high throughput deposition of different types of matrices on multiple samples 20. The XYZ position controller 41 for the XYZ translation stage 12 is able to move the matrices 17a up or down to reach the best position of matrix sublimation. The samples 20 can also be rotated (or translated) using the sample positioning system 36 multiple matrices in different matrix containers 17 may be heated to desired temperatures to obtain uniform coating of molecules from the solvent-free matrix mixtures.

The molecule guiding system 18 may be configured to have a single channel or multiple channels to provide for improved molecular coating, minimized matrix loss, and reduced contamination. The sample handling system 34 may be used to automatically or controllable move samples 20 onto the sample holders 19, while the matrix handling system 39 may be used to add certain amounts of matrices into the matrix containers 17.

The automatic dosing-pumping system 32 may be used to control the vacuum level and vapor components during the sublimation-condensation process for optimized deposition performance. A turbo pump may be employed in the pumping system 38 to generate ultra-high vacuum conditions (as low as $10^{-10}$ Torr) to control surface cleaning and repeated deposition.

The surface characterization system comprises a deposition monitoring system 33 and software running on the computer 40 that may be used to monitor the thickness and roughness of the deposited molecule layer and optimize deposition conditions. All sublimation-condensation and sample transfer processes may be automatically controlled by the computer 40 so that no user intervention is needed.

Figure 2A:
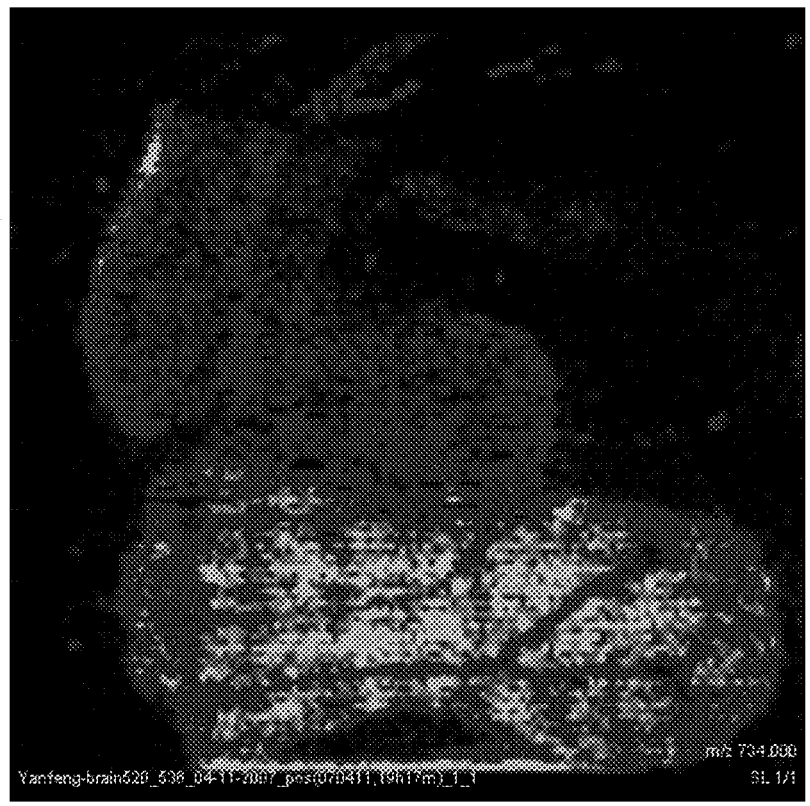
FIGS. 2a-2d are mass spectrometry images of lipid molecules in different brain sections obtained using the reduced-to-practice solvent-free matrix vapor deposition apparatus shown in FIG. 1.
Figure 2B:
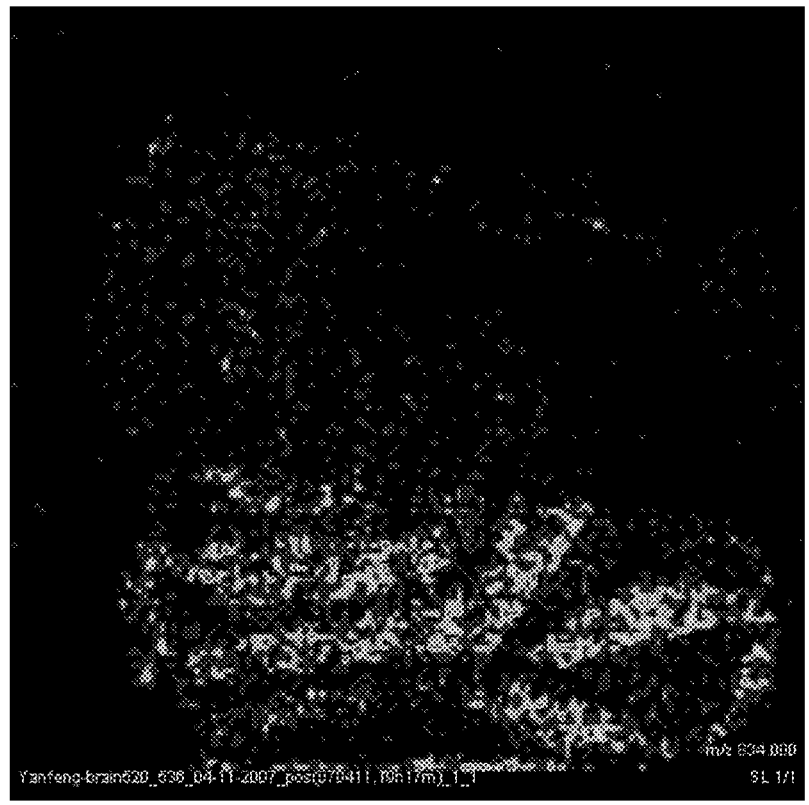
Figure 2C:
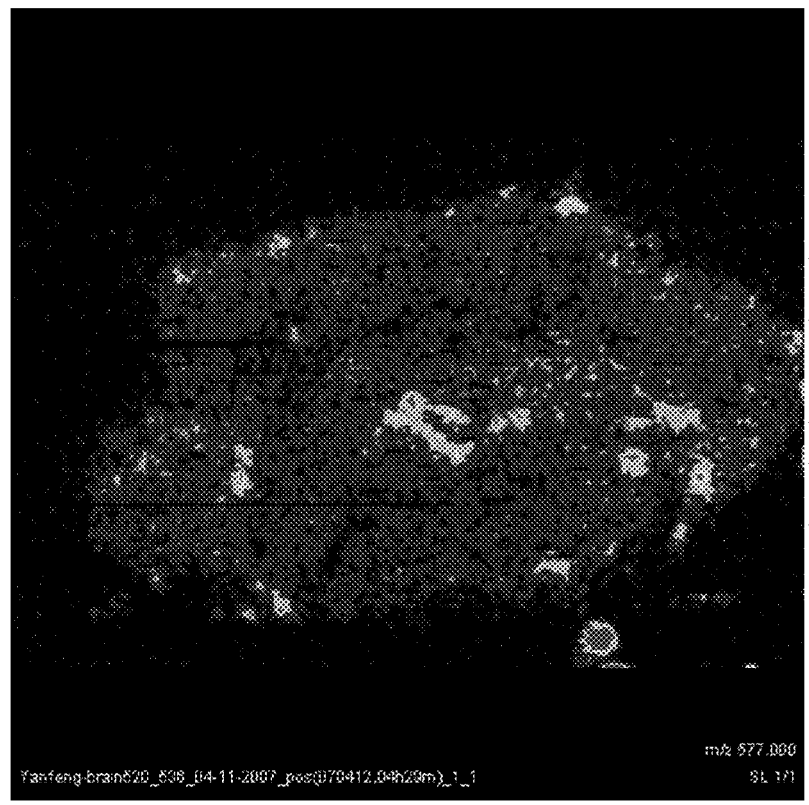
Figure 2D:
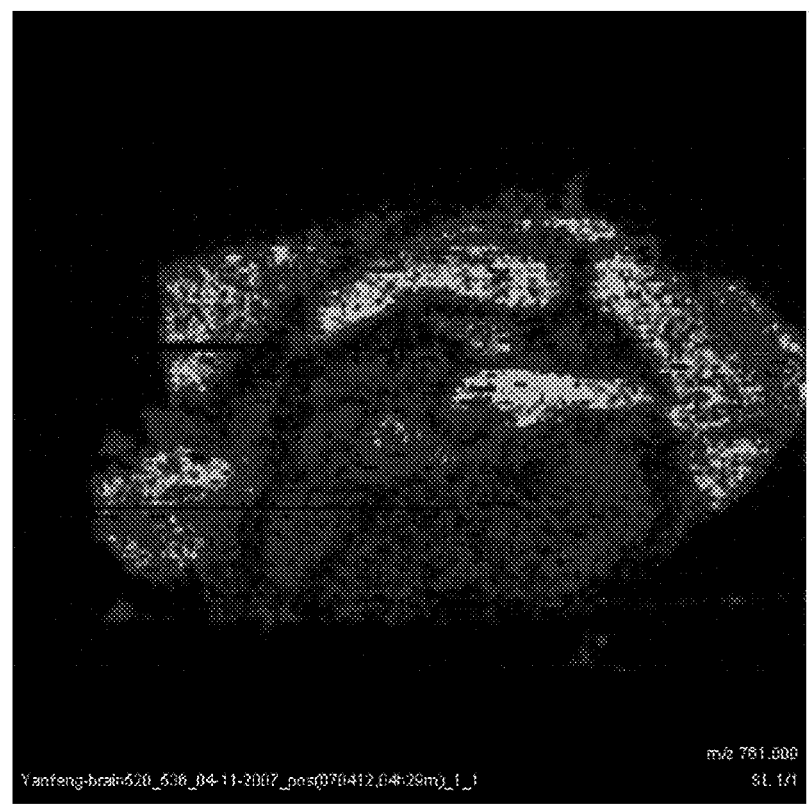

A useful example of the benefits provided by the solvent-free matrix vapor deposition apparatus 10 described above is the creation of excellent ion images of phospholipids likely derived from 16:0a/16:0-glycerophosphocholine (m/z 734.6), 16:0a/18:1-glycerophosphocholine (m/z 760.6), 18:0a/22:6-glycerophosphocholine (m/z 834.6), and a lipid fragment ion at m/z 577. Representative images showing mass spectrometry images of lipid molecules in different brain sections are illustrated in FIGS. 2a-2d. In particular, FIG. 2a shows m/z 734, FIG. 2b shows m/z 834, FIG. 2c shows m/z 577, and FIG. 2d shows m/z 761.

There are differences in definition and texture when comparing images of robotically spotted standards with different methods of matrix application that imply the occurrence of subtle spreading of lipids with ESI matrix deposition, and none using the gas phase matrix deposition as described herein. Signal intensity for a $[M+H]^+$ ion from a glycerol-phosphocholine standard was significantly enhanced and even more enhanced in samples with a sublimated matrix relative to samples with ESI matrix deposition. The gas phase solvent-free matrix deposition yields a higher quality and more reliable representation of in-situ phospholipid molecular species of mouse brain tissue sections than deposition by techniques utilizing solutions of matrix that are subsequently evaporated to crystallize the matrix.

For the purposes of completeness, FIG. 3 is a flow diagram that illustrates an exemplary solvent-free matrix deposition method 50. The exemplary solvent-free matrix deposition method 50 may be implemented as follows.

One or more solvent-free matrices 17 are disposed 51 within a vacuum chamber 11. One or more samples 20 are disposed 52 within the vacuum chamber 11 distal from the one or more solvent-free matrices 17. The vacuum chamber 11 is evacuated 53. Each solvent-free matrix 17 is individually heated 54 to a desired temperature to sublimate solvent-free molecules therefrom. Each sample 20 is individually cooled 55 to a desired temperature to deposit the sublimated solvent-free molecules on the samples 20. The relative positions of each solvent-free matrix 17 and each sample 20 is adjusted 56 to optimize deposition of the sublimated solvent-free molecules on the samples 20.

Optionally, the sublimated solvent-free molecules may be guided 57 toward the samples 20 to improve molecular coating of the samples 20, minimize matrix loss and reduced contamination. Optionally, additives are injected 58 into the chamber 11 to enhance matrix deposition. Optionally, the thickness and roughness of the deposited solvent-free molecules are monitored and characterized 59 to optimize deposition.

Thus, solvent-free matrix deposition apparatus and methods for use in imaging mass spectrometry have been disclosed. It is to be understood that the above-described embodiments are merely illustrative of some of the many specific embodiments that represent applications of the principles discussed above. Clearly, numerous and other arrangements can be readily devised by those skilled in the art without departing from the scope of the invention.

What is claimed is:

1. Molecule deposition apparatus comprising:
a vacuum chamber;
controllable matrix translation apparatus for controlling the position of solvent-free matrix material within the chamber whose molecules are to be deposited;
sublimation apparatus for sublimating the molecules from the solvent-free matrix material;
one or more solvent-free matrices whose position is controllable by the controllable translation apparatus;
one or more samples that are separated from the one or more solvent-free matrices;
condensation apparatus for individually cooling the samples to deposit the sublimated molecules on the samples; and
controllable sample translation apparatus for controlling the position of the samples within the chamber.

2. The apparatus recited in claim 1 further comprising a masking system for patterning deposition of the solvent-free molecules on the sample.

3. The apparatus recited in claim 1 further comprising molecule guiding apparatus for confining the sublimated molecules within the chamber so that they more efficiently deposit on the one or more samples.

4. The apparatus recited in claim 1 further comprising rotatable sample holding apparatus for holding and moving the one or more samples to allow deposition of molecules on multiple samples at substantially the same time.

5. The apparatus recited in claim 1 further comprising rotatable matrix holding apparatus for holding and moving a plurality of solvent-free matrices to create a homogenous mixture of molecules that are deposited onto the one or more samples.

6. The apparatus recited in claim 1 further comprising a dosing-pumping system that controls pressure in the chamber and permits addition of desired substances into the chamber.

7. The apparatus recited in claim 1 further comprising a computer coupled to the controllable matrix translation apparatus, the sublimation apparatus, the condensation apparatus, and the controllable sample translation apparatus, and a software program that runs on the computer, for providing automated deposition of solvent-free molecules on the samples.

8. The apparatus recited in claim 1 further comprising a surface characterization system for monitoring deposition of the solvent-free molecules on the one or more samples to determine the thickness an roughness of the deposited molecules.

9. Molecule deposition apparatus comprising:
a vacuum chamber;
controllable matrix translation apparatus for controlling the position of solvent-free matrix material within the chamber whose molecules are to be deposited;
sublimation apparatus for sublimating the molecules from the solvent-free matrix material;
a plurality of solvent-free matrices whose positions are controllable by the controllable translation apparatus;
one or more samples that are separated from the one or more solvent-free matrices;
rotatable sample holding apparatus for holding and moving the one or more samples to allow deposition of molecules on multiple samples at substantially the same time;
condensation apparatus for individually cooling the one or more samples to deposit the sublimated molecules on the samples; and
controllable sample translation apparatus for controlling the position of the samples within the chamber.

10. Molecule deposition apparatus comprising:
a vacuum chamber;
controllable matrix translation apparatus for controlling the position of solvent-free matrix material within the chamber whose molecules are to be deposited;
sublimation apparatus for sublimating the molecules from the solvent-free matrix material;
a plurality of solvent-free matrices whose positions are controllable by the controllable translation apparatus;
rotatable matrix holding apparatus for holding and moving the plurality of solvent-free matrices to create a homogenous mixture of molecules for deposition onto samples;
one or more samples that are separated from the one or more solvent-free matrices;
condensation apparatus for individually cooling the one or more samples to deposit the sublimated molecules on the samples; and
controllable sample translation apparatus for controlling the position of the samples within the chamber.

11. The apparatus recited in claim 10 further comprising rotatable matrix holding apparatus for holding and moving the plurality of solvent-free matrices to create a homogenous mixture of molecules for deposition onto samples.

12. A molecule deposition method comprising:
disposing one or more solvent-free matrices within a vacuum chamber;
disposing one or more samples within the vacuum chamber distal from the one or more solvent-free matrices;
evacuating the vacuum chamber;
individually heating each solvent-free matrix to a desired temperature to sublimate solvent-free molecules therefrom;
individually cooling each sample to a desired temperature to deposit the sublimated solvent-free molecules on each sample;
adjusting the relative positions of each solvent-free matrix and each sample to optimize deposition of the sublimated solvent-free molecules on the samples.

13. The method recited in claim 12 further comprising substantially simultaneously depositing molecules from the same solvent-free matrix onto multiple samples.

14. The method recited in claim 12 further comprising substantially simultaneously depositing a homogeneous mixture of molecules derived from different solvent-free matrices onto one or more samples.

15. The method recited in claim 12 further comprising guiding the sublimated solvent-free molecules toward the samples to improve molecular coating of the sample, minimize matrix loss and reduced contamination.

16. The method recited in claim 12 further comprising injecting additives into the chamber to enhance deposition and promote surface cleaning.

17. The method recited in claim 12 further comprising monitoring and characterizing the thickness and roughness of the deposited solvent-free molecules to optimize deposition.

18. The method recited in claim 12 further comprising masking the one or more samples to deposit patterns of free molecules on the one or more samples.

* * * * *

UNITED STATES PATENT AND TRADEMARK OFFICE
CERTIFICATE OF CORRECTION

PATENT NO. : 7,880,139 B2  
APPLICATION NO. : 12/154912  
DATED : February 1, 2011  
INVENTOR(S) : Chen et al.

Page 1 of 1

It is certified that error appears in the above-identified patent and that said Letters Patent is hereby corrected as shown below:

Title Page, At Section (73) of the patent, please add the following assignee:

--Regents of the University of Colorado--

Column 1, line, 8, please insert the following paragraph

--STATEMENT REGARDING FEDERALLY SPONSORED
RESEARCH OR DEVELOPMENT

This invention was made with Government support under Agreement No. GM-069338, awarded by the National Institutes of Health. The Government has certain rights in the invention.--

Signed and Sealed this
Tenth Day of July, 2012

David J. Kappos
*Director of the United States Patent and Trademark Office*